United States Patent [19]

Crews et al.

[11] Patent Number: 4,943,589

[45] Date of Patent: Jul. 24, 1990

[54] ANTHELMINTIC DYSININS OF MARINE ORIGIN

[75] Inventors: Phillip Crews, Santa Cruz; Thomas R. Matthews, Los Gatos; Paul Horton, Santa Cruz, all of Calif.

[73] Assignees: Syntex (U.S.A.) Inc., Palo Alto; The Regents of the Univ. of California, Berkeley, both of Calif.

[21] Appl. No.: 263,261

[22] Filed: Oct. 27, 1988

[51] Int. Cl.$^5$ ..................... A61K 31/34; C07D 407/12
[52] U.S. Cl. ..................................... 514/468; 549/458
[58] Field of Search ......................... 549/458; 514/468

[56] References Cited

PUBLICATIONS

Capon et al., *J. Natural Products* (1987) 50(6):1136–1137.
Carte et al. *J. Organ. Chem.* (1986) 51:3528–3523.
Anderson et al., *Tetrahedron* (1982) 38(13) 1875–1879.
Wells et al., *IUPAC Internatl. Sump. Chem Natural Products* 2:104–107.
Cardellina II et al., *J. Natural Products* (1984) 47(1):76–83.
Wells et al., *Australian J. Chem* (1982) 35:95–103.
Wells et al., *Tetrahendron Letters* (1978) 49:4951–4954.
Pietra et al., *Helvetica Chimica Acta* (1985) 68:1276–1282.
Hirota et al., *Chem. Letters* (1987) 10:2079–2080.
Albizati et al., ORGN abstract No. 385, American Chemical Society Meeting, Los Angeles, Sep., 1988.
Dodds et al., *J. Amer. Chem Soc.* (1988) 110:577–583.
Jenkinse et al., *Z. Parasitenkunde* (1980) 63:261–269.
Greene et al., *J. Organ. Chem.* (1978) 43(22):4377–4379.
Gregson et al., *Aust. J. Chem.* (1976) 29:2037–2048.
Ranganathan et al., *Synthesis* (May, 1977) pp. 289–296.

*Primary Examiner*—Mary C. Lee
*Assistant Examiner*—Jacqueline Haley
*Attorney, Agent, or Firm*—Irell & Manella

[57] ABSTRACT

This invention is directed to a method for treating helminthiasis which comprises administering to an animal in need thereof an anthelmintically effective amount of a compound of Formula (I):

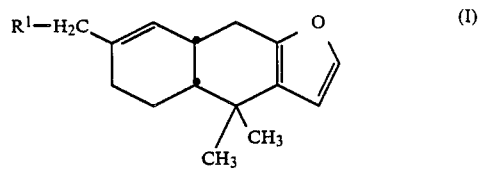

where
$R^1$ is hydrogen or $-SR^2$,
wherein
$R^2$ is hydrogen, $-C(O)-CH_3$, or

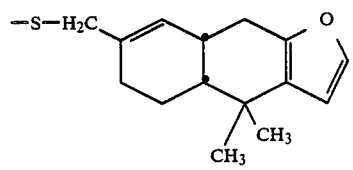

or a pharmaceutically acceptable salt thereof. This invention is also directed to a composition for treating helminthiasis in an animal which comprises a pharmaceutically acceptable excipient and an anthelmintically effective amount of a compound of Formula (I). This invention is also directed to novel compounds of Formula (I) wherein $R^2$ is

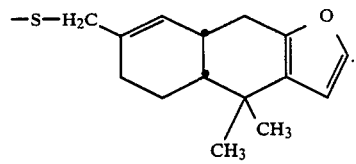

13 Claims, No Drawings

ANTHELMINTIC DYSININS OF MARINE ORIGIN

STATEMENT OF GOVERNMENT INTEREST

This invention was made with Government support under the National Sea Grant College Program, project number R/MP-41 awarded by the National Oceanic and Atmospheric Administration. The Government has certain rights in this invention.

BACKGROUND OF THE INVENTION

1. Field of the Invention

This invention relates to a method for treating helminthiasis in animals by administering compounds of the invention. This invention also relates to compositions for treating helminthiasis in animals that are comprised of compounds of the invention and pharmaceutically acceptable excipients. This invention also relates to novel compounds of Formula (I).

RELATED DISCLOSURE

Certain sesquiterpene derivatives of marine origin, e.g., furodysinin, thiofurodysinin, and thiofurodysinin acetate, are known in the art. However, no pharmaceutical utility has been reported for such derivatives. See, for example, the following:

(a) "Thiofurodysinin, A Sulfur-Containing Furanosesquiterpene from the Marine Sponge *Dysidea Avara*," R. Capon et al., *Journal of Natural Products*, 1987, vol. 50, No. 6, pp 1136–1137, where the isolation of furodysinin, thiofurodysinin acetate and thiofurodysinin is described;

(b) "Metabolites of the Nudibranch *Chromodoris funerera* and the Singlet Oxygen Oxidation Products of Furodysin and Furodysinin," B. Carté et al., *Journal of Organic Chemistry*, 1986, Vol. 51, pp. 3528–3532 where it is postulated that certain sponge-eating nudibranches (molluscs) modify sesquiterpene derivatives found in sponges to produce useful metabolites;

(c) "Terpenoids From the Dorid Nudibranch *Cadlina Luteomarginata*," R. J. Anderson et al, *Tetrahedron*, 1982, Vol. 38, No. 13, pp. 1875–1879, where furodysinin is reported as an extract of a sponge-eating nudibranch;

(d) "Novel Metabolites From the Sponge Genus Dysidea,"R. J. Wells et al., *IUPAC International Symposium on Chemistry of Natural Products* 11th, Volume 2. pp. 104–107, where isolation of thiofurodysinin acetate and furodysinin is described;

(e) "Sesquiterpenes From the Sponge *Dysidea Etheria* and the Nudibranch *Hypselodoris Zebra*," J. Cardellina II et al., *Journal of Natural Products*. 1984, Vol. 47, No. 1, pp. 76–83, where the isolation of furodysinin is described;

(f) "New Furano-Sesquiterpenes from the Sponge *Dysidea herbacea*," R. J. Wells et al., *Australian Journal of Chemistry*, 1982, Vol. 35, pp. 95–103, where the isolation of furodysinin and thiofurodysin acetate is described;

(g) "Two Sesquiterpene Furans With New Carbocyclic Ring Systems and Related Thiol Acetates From a Species of the Sponge Genus Dysidea," R. J. Wells et al., *Tetrahedron Letters*, 1978, No. 49, pp. 4951–4954, where the isolation of furodysinin, and thiofurodysinin acetate is described;

(h) "New Furano-sesquiterpenoids from Mediterranean Sponges," F. Pietra et al., *Helvetica Chimica Acta*, 1985, Volume 68, pp. 1276–1282 where the isolation of an enantiomer of furodysinin is described; and (i) "Total Synthesis of (±)-Furodysin and (±)-Furodysinin," H. Hirota et al., *Chemistry Letters*. 1987, No. 10, pp. 2079–2080; where the synthesis of racemic forms of furodysinin is described; and (j) "Synthesis of Marine Furanosesquiterpenes. New Utilizations of Camphor Derivatives," K. Albizati et al., ORGN Abstract No. 385, American Chemical Society Meeting, Los Angeles, September, 1988; where the synthesis of enantiomers of furodysinin is described.

The disclosure of the these and all other documents referred to in this specification are incorporated herein by reference.

SUMMARY OF THE INVENTION

One aspect of the invention is a method for treating helminthiasis in an animal, which method comprises administering to an animal in need thereof an anthelmintically effective amount of a single enantiomer or a mixture of enantiomers of a compound of Formula (I):

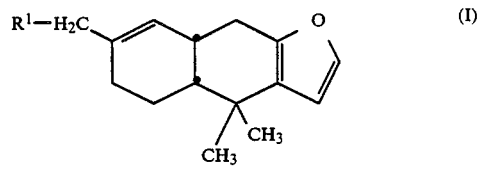

where
$R^1$ is hydrogen or $-SR^2$,
wherein
$R^2$ is hydrogen, $-C(O)-CH_3$, or

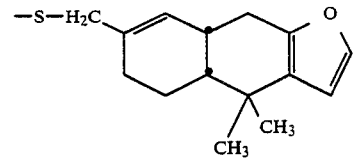

or a pharmaceutically acceptable salt thereof.

Another aspect of the invention are novel compounds of Formula (I) wherein $R^2$ is

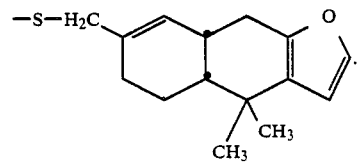

Another aspect of the invention is a composition for treating helminthiasis which comprises an anthelmintically effective amount of a single enantiomer or a mixture of enantiomers of a compound of Formula (I) and a pharmaceutically acceptable excipient.

DETAILED DESCRIPTION OF THE INVENTION

Definitions

As used in the specification and appended claims, unless specified to the contrary, the following terms having the meaning indicated:

When a chemical formula is depicted with the bridgehead hydrogens represented by a closed circle, e.g.,

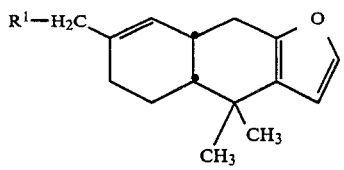

it represents that the hydrogens are cis to each other, for example, both hydrogens are on the α-side of the reference plane, or both hydrogens are on the β-side of the reference plane.

The numbering system used in naming the compounds of the present invention is illustrated below:

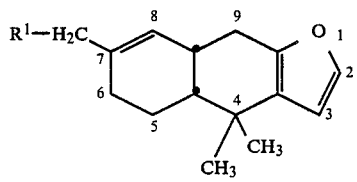

The compounds of this invention possess asymmetric centers and thus can be extracted or produced as racemic or non-racemic mixtures or as individual enantiomers. It is understood that the racemic or non-racemic mixtures and the individual enantiomers are encompassed within the scope of the present invention. Therefore, the term "mixture" refers to both a racemic and a non-racemic mixture of enantiomers. The term "furodysinin" refers to a compound of Formula (I) wherein $R^1$ is hydrogen, i.e., 4,4,7-trimethyl-cis-4,4a,5,6,8a,9-hexahydronaphtho[2,3-b]furan.

The term "ent-furodysinin" refers to the levorotatory enantiomer of furodysinin.

The term "thiofurodysinin" refers to a compound of Formula (I) wherein $R^1$ is —$SR^2$ where $R^2$ is hydrogen, e.g., 4,4-dimethyl-7-thiolmethyl-cis-4,4a,5,6,8a,9-hexahydronaphtho[2,3-b]furan.

The term "ent-thiofurodysinin" refers to the levorotatory enantiomer of thiofurodysinin. The term "thiofurodysinin acetate" refers to a compound of Formula (I) wherein $R^1$ is —$SR^2$ where $R^2$ is —C(O)—CH3, i.e., (4,4-dimethyl-cis-4,4a,5,6,8a,9-hexahydronaphtho[2,3-b]furan-7-yl)methyl S-thioacetate.

The term "ent-thiofurodysinin acetate" refers to the levorotatory enantiomer of thiofurodysinin acetate.

The term "furodysinin disulfide" refers to a compound of Formula (I) wherein $R^1$ is —$SR^2$ where $R^2$ is

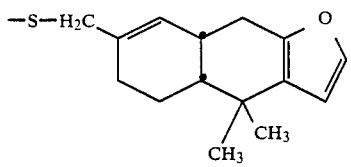

i.e., bis[methyl(4,4-dimethyl-cis-4,4a,5,6,8a,9-hexahydronaphtho[2,3-b]furan-7-yl)]disulfide.

The term "ent-furodysinin disulfide" refers to the levorotatory enantiomer of furodysinin disulfide.

The term "pharmaceutically acceptable" as used herein includes that which is acceptable for veterinary use, and is not limited to suitability for human use.

The term "pharmaceutically acceptable salt" refers to salt of the subject compounds which possesses the desired pharmacological activity and which is neither biologically nor otherwise undesirable. This salt is an acid addition salt formed with inorganic acids such as hydrochloric acid, hydrobromic acid, sulfuric acid, nitric acid or phosphoric acid; or organic acids such as acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

The term "animal" includes humans and all domestic and wild mammals and fowl, including, without limitation, cattle, horses, swine, sheep, goats, dogs, cats, rabbits, deer, mink, chickens, ducks, geese, turkeys, game hens, and the like.

The term "treatment" as used herein covers any treatment of a disease in an animal and includes:

(i) preventing the disease from occurring in an animal which may be predisposed to the disease but has not yet been diagnosed as having it;

(ii) inhibiting the disease, i.e., arresting its development; or (iii) relieving the disease, i.e., causing regression of the disease.

The term "anthelmintically effective amount" refers to that amount which, when administered to an animal in need thereof is sufficient to effect treatment, as defined above. Furthermore, an "anthelmintically effective amount" of a compound of Formula (I) for treating helminthiasis will vary depending on the species of helminth, the severity of the infection, and the animal to be treated, but may be determined routinely by one of ordinary skill in the art.

Preferred Embodiments

One aspect of the invention is a method for treating helminthiasis, which method comprises administering to an animal in need thereof an anthelmintically effective amount of a single enantiomer or a mixture of enantiomers of a compound of Formula (I). A presently preferred method is the method wherein $R^1$ is hydrogen. Another presently preferred method is the method wherein $R^2$ is —C(O)—CH3. Another presently preferred method is the method wherein $R^2$ is hydrogen. Another presently preferred method is the method wherein $R^2$ is

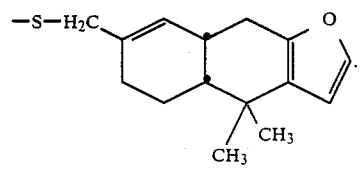

The presently most preferred methods are the methods wherein the compound of Formula (I) is ent-furodysinin, i.e., (−)-4,4,7-trimethyl-cis-4,4a,5,6,8a,9-hexahydronaphtho[2,3-b]furan; ent-thiofurodysinin acetate, i.e., (−)-(4,4-dimethyl-cis-4,4a,5,6,8a,9-hexahydronaphtho[2,3-b]furan-7-yl)methyl S-thioacetate; or ent-furodysinin disulfide, i.e., (−)-bis[methyl(4,4- dimethyl-cis-4,4a,5,6,8a,9-hexahydronaphtho[2,3-b]furan-7-yl)]disulfide.

Another aspect of the invention is a composition for treating helminthiasis in an animal which comprises an anthelmintically effective amount of a single enantiomer or a mixture of enantiomers of a compound of Formula (I) and a pharmaceutically acceptable excipient. A presently preferred composition is the composition wherein $R^1$ is hydrogen. Another presently preferred composition is the composition wherein $R^2$ is —C(O)—CH$_3$. Another presently preferred composition is the composition wherein $R^2$ is hydrogen. Another presently preferred composition is the composition wherein $R^2$ is

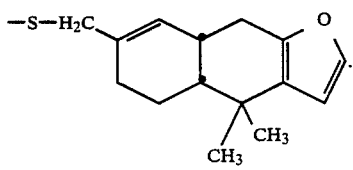

The presently most preferred compositions are the compositions wherein the compound of Formula (I) is ent-furodysinin, i.e., (−)-4,4,7-trimethyl-cis-4,4a,5,6,8a,9-hexahydronaphtho[2,3-b]furan; ent-thiofurodysinin acetate, i.e., (−)-(4,4-dimethyl-cis-4,4a,5,6,8a,9-hexahydronaphtho[2,3-b]furan7-yl)methyl S-thioacetate; or ent-furodysinin disulfide, i.e., (−)-bis[methyl(4,4-dimethyl-cis-4,4a,5,6,8a,9-hexahydronaphtho[2,3-b]furan-7-yl)]disulfide.

Another aspect of the invention are the compounds of Formula (I) wherein $R^2$ is

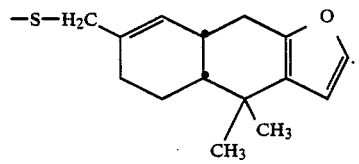

A presently preferred embodiment is the compound of Formula (I) wherein $R^2$ is

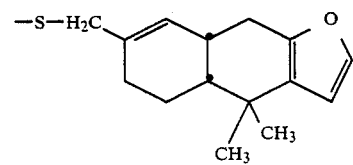

that is at least 90% pure, preferably at least 95% pure, and most preferably at least 99% pure. A presently most preferred embodiment is the levorotatory enantiomer of the compound of Formula (I) wherein $R^2$ is

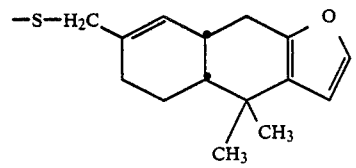

namely, ent-furodysinin disulfide, i.e., (−)-bis[methyl(4,4-dimethyl-cis-4,4a,5,6,8a,9-hexahydronaphtho[2,3-b]furan-7-yl)]disulfide.

Methods of Preparation:

Certain compounds of Formula (I) can be isolated from an abundant marine sponge, tentatively identified as *Dysidea herbacea* (order Dictyoceratida; family Dysideidae) native to the waters surrounding the Fiji Islands. The sponge has the following characteristics, by which one of ordinary skill in the art may recognize the appropriate sponge and distinguish it from others:

The sponge can be massive and flat to tubular in shape. It has large and elongated flagellate chambers and its fibers consist mostly of foreign material (detritus). The color of the sponge may vary from light purple to tan. This is in contrast to the dark green or ochre described for Australian sponges that are similarly tentatively identified as *D. herbacea*. See, for example, Wells, R. J. et al., *Australian Journal of Chemistry.* 9182, Vol. 35, pp. 95–103. Color variations between members of the same species may be due to the symbionts of the sponge. See, for example, Berthold, R. J. et al., *Phycologia*, 1982, Vol. 21, pp. 327–335.

A fresh *Dysidea herbacea* sponge, collected from the Benga lagoon in the Fiji Islands, is cut into small pieces and immersed in CH$_2$Cl$_1$ for 24 hrs. The CH$_2$Cl$_2$ is then decanted. The sponge is next soaked with MeOH for 24 hrs. Afterwards, the MeOH is decanted and combined with the CH$_2$Cl$_2$. The solvents are then evaporated to yield a crude oil. A portion of the oil is then successively partitioned between equal volumes of methanol (wet, percent adjusted to produce a biphase solution) and a solvent series of hexane, carbon tetrachloride, and methylene chloride. The hexane partition fraction is then chromatographed (normal phase flash column chromatography) using a gradient of 5:95 ethyl acetate:-hexane to 100% ethyl acetate. Fractions containing compounds of similar polarity are monitored by thin-layer chromatography (TLC) and nuclear magnetic resonance (NMR). Fractions displaying lowfield signals in the $^{13}$C NMR spectra are combined and further purified by preparative normal phase HPLC to yield the levorotatory enantiomers of a compound of Formula (I) wherein $R^1$ is —SR$^2$, i.e., ent-thiofurodysinin acetate and ent-furodysinin disulfide. Ent-thiofurodysinin acetate is further reduced to a compound of Formula (I) wherein $R^1$ is hydrogen, i.e., ent-furodysinin.

Certain compounds of Formula (I) may also be prepared by following the Reaction Scheme below.

REACTION SCHEME

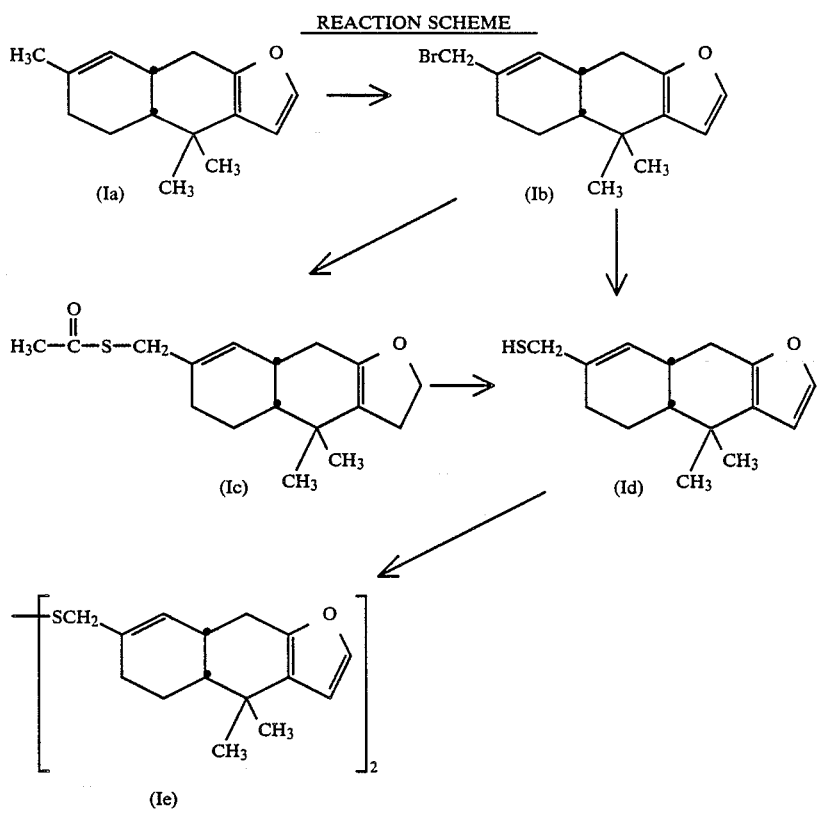

The compounds of Formula (Ia) are brominated using n-bromosuccinimide (available, inter alia., Aldrich Chemical Co.) to form compounds of Formula (Ib). The compounds of Formula (Ib) are then reacted with potassium thiolacetate (available, inter alia, Aldrich Chemical Co.) to form compounds of Formula (Ic). The compounds of Formula (Ic) are then hydrolyzed under basic conditions using, for example, potassium hydroxide, to form compounds of Formula (Id). Alternatively, the compounds of Formula (Ib) are then reacted with thiourea to form compounds of Formula (Id). The compounds of Formula (Id) are then dissolved in a solution of sodium methoxide in methanol and then treated with oxygen to form compounds of Formula (Ie). This last step is discussed in more detail in *J. Org. Chem.*, Vol. 43, No. 22, 1978, pp. 4377–4379.

The absolute configuration of compounds of Formula I is determined by analogy to work carried out by Olivier Albizati et al., where it was determined that the brigehead hydrogens of ent-furodysinin are in the β-position (see, Albizati, et al., supra). Since we had reduced ent-thiofurodysinin acetate to ent-furodysinin by a process that would not alter the configuration of the bridgehead hydrogens, it is determined that the bridgehead hydrogens of ent-thiofurodysinin acetate are also in the β-positon.

Furthermore, the synthesis described above will not alter the configuration of the bridgehead hydrogens of the resulting products. Therefore, if ent-furodysinin is is used as the starting material in the synthesis, the resulting products would all have the bridgehead hydrogens in the β-position. Thus, the absolute configuration of the compounds of Formula (I) is determined.

Administration and Formulation:

One aspect of the present invention relates to pharmaceutical and veterinary compositions useful in the treatment of helmintic infection, comprising an anthelmintically effective amount of a compound of Formula (I), or a pharmaceutically acceptable acid addition salt thereof, in admixture with a pharmaceutically acceptable non-toxic carrier. Compounds of Formula (I) are effective against nematodes and other helminths, such as *Nippostrongylus braziliensis,* at concentrations of about 5 µg/mL to about 250 µg/mL.

In view of the foregoing as well as in consideration of the degree of severity of the condition being treated, age of subject and so forth, all of which factors are determinable by routine experimentation by one skilled in the art, the effective dosage in accordance herewith can vary over a wide range. In general terms, an effective amount of a compound of Formula (I) for the treatment of helminthiasis will range from about 1 to about 100 mg/Kg.

Useful pharmaceutical carriers for the preparation of the pharmaceutical compositions hereof can be solids, liquids, gels, creams, ointments, and the like. Thus, the compositions can take the form of tablets, pills, capsules, powders, sustained release Formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

In the practice of the above described method of the present invention an anthelmintically effective amount of the compound of Formula (I) or a pharmaceutical composition containing same is administered via any of the usual and acceptable methods known in the art, either singly or in combination with another compound or compounds of the present invention or other pharmaceutical agents. These compounds or compositions can thus be administered orally or intraruminally, systemically (e.g., transdermally, intranasally or by suppository), topically, or parenterally (e.g., intramuscularly, subcutaneously and intravenously), and can be administered either in the form of solid or liquid dosages including tablets, solutions, suspensions, aerosols, and the like, as discussed in more detail above. It is preferred to administer compounds of Formula (I) orally when treating helminth infestations.

The formulation can be administered in a single unit dosage form for continuous treatment or in a single unit dosage form ad libitum when relief of symptoms is specifically required.

The following specific examples are provided as a guide to assist in the practice of the invention, and are not intended as a limitation on the scope of the invention.

EXAMPLE 1
(Extraction)

Certain compounds of Formula (I) were isolated from a sponge tentatively identified as *Dysidea herbacea* (order Dictyoceratida: family Dysideidae), which is native to the waters surrounding the Fiji Islands. The sponge has the following characteristics, by which one of ordinary skill in the art may recognize the appropriate sponge and distinguish it from others:

The sponge can be massive and flat to tubular in shape. It has large and elongated flagellate chambers and its fibers consist mostly of foreign material (detritus). The color of the sponge may vary from light purple to tan.

The sponge was found at a depth of approximately 30 to 60 feet in the Benga Lagoon, Fiji Islands.

A fresh *Dysidea herbacea* sponge was cut into small pieces and immersed in $CH_2Cl_2$ for 24 hrs. The $CH_2Cl_2$ was then decanted. The sponge was next soaked with MeOH for 24 hrs. The MeOH was then decanted and combined with the $CH_2Cl_2$. The solvents were then evaporated to yield a crude oil extract (14.27 g). Compounds of Formula (I) were components in the extract, and were detected using $^{13}C$ NMR. A portion of the extract was then successively partitioned between equal volumes (500 ml of aq MeOH, % adjusted to produce a biphase solution) and a solvent series of hexane (4.38 g), $CCl_4$ (1.71 g), and $CH_2Cl_2$ (1.36 g). The hexane partition fraction was then chromatographed (normal phase flash column chromatography) using a gradient of 5:95 ethyl acetate:hexane to 100% ethyl acetate. Fractions containing compounds of similar polarity were monitored by thin-layer chromatography and NMR. Fractions displaying lowfield signals in the $^{13}C$ NMR spectra were combined and further purified by preparative normal phase HPLC (Regis 10μ-silica column, hexane:ethyl acetate/5:95) to yield ent-thiofurodysinin acetate, i.e., (—)-(4,4-dimethyl-cis-4,4a,5,6,8a,9-hexahydronaphtho[2,3-b]furan-7-yl)methyl S-thioacetate (0.134 g) and ent-furodysinin disulfide, i.e., (—)-bis[methyl(4,4-dimethyl-cis-4,4a,5,6,8a,9-hexahydronaphtho[2.3-b]furan-7-yl)]disulfide (0.073 g).

A. Ent-thiofurodysinin acetate displays the following characteristics:
Molecular formula: $C_{17}H_{22}O_2S$.
Chemical formula:

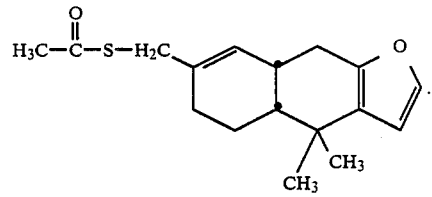

Optical Rotation: $[\alpha]_D^{20} = -34.6°$ (c=0.03, benzene).

B. Ent-furodysinin disulfide displays the following characteristics:
Physical State: Viscous Oil.
Molecular formula: $C_{30}H_{38}O_2S_2$.
Chemical formula:

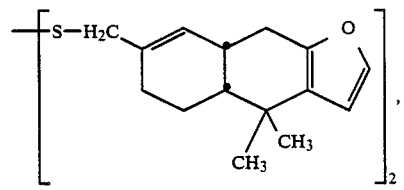

Optical Rotation: $[\alpha]_D^{20} = -27.8°$ (c=0.009, benzene)

NMR Data: $^{13}C$ δ's at 75 MHz, δ's and J's at 300 MHz. Solvent used was $CDCl_3$. Atom number indicated in brackets: [1] 131.1, 5.88 (d, J=5.4); [2] 132.8; [3]28.7, 2.23 (m, 2H); [4]19.2, 1.78 (m), 1.25 (m); (5) 44.4, 1.58 (dt, J=13.5, 3.0); [6] 34.0; [7] 124.7; [8] 147.0; [9] 27.4, 27.8 (dd, J=17.7,6.3), 2.33 (dd, J=8.3,12.3); [10] 31.5, 2.78 (m); [11] 46.3, 3.29 (d, J=12.6), 3.22 (d, J=12.9); [12] 108.1, 6.24 (d, J=1.5); [13] 140.6, 7.22 (s); [14,15] 26.1,32.8, 1.21 (s,3H), 1.19 (s, 3H).

Mass Spectromety Data: Low resolution electron impact mass spectrometry (LREIMS): m/z (%); 494(40), 462(14), 430(13), 280(55), 214(81), 216(81), 159(66), 122(100). Chemical ionization mass spectrometry (CIMS): (isobutane) m/z (%); 552(23), 495(50), 468(16), 305(232), 281(43), 273(63), 247(100), 217(71), 215(100).

EXAMPLE 2

To a solution of ent-thiofurodysinin acetate (0.2143 g) in ethanol (5.0 mL) was added a suspension of Raney Nickel (1.0 g) at room temperature. The mixture was stirred for 10 minutes and then filtered. Solvent was then removed in vacuo from the filtrate. The resulting product was then purified by normal phase HPLC (15% ethyl acetate in hexane) to yield ent-furodysinin, i.e., (—)-4,4,7-trimethyl-cis-4,4a,5,6,8a,9-hexahydronaphtho[2,3-b]furan, 0.1348 g.

Ent-furodysinin displays the following characteristics:
Molecular formula: $C_{15}H_{20}O$.
Chemical formula:

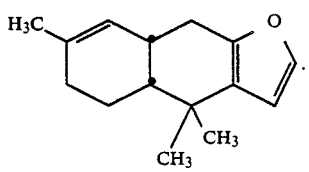

Optical Rotation: $[\alpha]_D^{20} = -9.9°$ (c=0.04, benzene).

EXAMPLE 3

(Formulations)

The following example illustrates the preparation of representative pharmaceutical formulations containing an active compound of Formula (I):

(A) The following formulation is suitable for intravenous administration, oral drench, and (in the treatment of large ruminants) intraruminal injection.

| I.V. Formulation | | |
|---|---|---|
| Compound of Formula (I) | | 1.0 mg |
| Propylene glycol | | 20.0 g |
| Polyethylene glycol 400 | | 20.0 g |
| Tween ® 80 | | 1.0 g |
| 0.9% Saline solution | qs | 100.0 mL |

The compound of Formula (I) is dissolved in propylene glycol, polyethylene glycol 400 and Tween ® 80. A sufficient quantity of 0.9% saline solution is then added with stirring to provide 100 mL of the I.V. solution which is filtered through a 0.2 micron membrane filter and packaged under sterile conditions.

(B) A tablet formulation is prepared as follows:

| | Parts |
|---|---|
| Compound of Formula (I) | 5.0 |
| Magnesium stearate | 0.75 |
| Starch | 0.75 |
| Lactose | 29.0 |
| PVP (polyvinylpyrrolidone) | 0.75 |

The above ingredients are combined and granulated using methanol. The formulation is then dried and formed into tablets (containing 500 mg of active compound) with an appropriate tabletting machine.

EXAMPLE 4

(In Vitro Anthelmintic Activity)

To obtain the fourth larval stage (L4) of *Nippostronzylus brasiliensis*, rats were inoculated with 6,500 to 6,750 *N. brasiliensis* third stage larvae subcutaneously. Seventy-two hours later the rats were sacrificed and the fourth stage larvae harvested. Compounds of Formula (I) were tested at 50 μg/mL against the fourth larval stage of *N. brasiliensis* at approximately 50 L4/well. This mixture was incubated at 37° C. for a total of seven days and then read for activity Parameters used to determine drug activity were motility, viability, and the ability of fourth stage larvae to molt to the adult, i.e., cast formation. A compound was defined as active if
(1) cast formation was reduced by 50 percent or more; or
(2) viability and motility together were reduced 50 percent or more.

The results are illustrated in the following Table 1:

TABLE 1

| Compound | Conc. | PERCENT REDUCTION COMPARED TO CONTROL | | |
|---|---|---|---|---|
| | | Casts | Viability | Motility |
| Compound A | 50 μg/ml | 71% | 52% | 50% |
| Compound B | <50 μg/ml | 62% | 3% | 0 |
| Compound C | 50 μg/ml | 92% | 46% | 65% |

Compound A is ent-thiofurodysinin acetate, i.e., (−)-(4,4-dimethyl-cis-4,4a,5,6,8a,9-hexahydronaphtho[2,3-b]furan-7-yl)methyl S-thioacetate.
Compound B is ent-furodysinin disulfide, i.e., (−)-bis[methyl(4,4-dimethyl-cis-4,4a,5,6,8a,9-hexahydronaphtho[2,3-b]furan-7-yl)] disulfide.
Compound C is ent-furodysinin, i.e., (−)-4,4,7-trimethyl-cis-4,4a,5,6,8a,9-hexahydronaphtho[2,3-b]furan.
Percent cast reduction was determined by the following:
$$\frac{\text{No. of untreated casts} - \text{No. of treated casts}}{\text{Number of untreated casts}} \times 100$$
Percent viability reduction was determined by the following:
$$\frac{\text{No. of untreated worms} - \text{No. of treated worms}}{\text{Number of untreated worms}} \times 100$$
Percent motility reduction was subjective evaluation.

EXAMPLE 5

(In Vivo Anthelmintic Activity)

Male Swiss-Webster mice were challenged with a mixed helminth infection of *Nematospiroides dubius* and *Hymenolepis nana*. Starting with 24 hours after infection, the mice were treated for eighteen (18) days ad lib with a mixture of compounds of Formula (I) mixed in the food at the concentrations shown in the following Table 2. Each treatment group had 4 mice. Mice were sacrificed on day nineteen (19) to examine parasite burden in the intestine. The results are illustrated in the following Table 2:

TABLE 2

| Compound | Conc.(ppm) | Deaths | PERCENT REDUCTION OF PARASITES | |
|---|---|---|---|---|
| | | | *N. dubius* | *H. nana* |
| Compound A | 422 | 0 | 83 | 42 |
| Compound B | 200 | 0 | 59 | 0 |

Compound A is a mixture of ent-thiofurodysinin acetate, i.e. (-)-(4,4-dimethyl-cis-4,4a,5,6,8a,9-hexahydronaphtho[2,3-b]furan-7-yl)methyl S-thioacetate, and ent-furodysinin disulfide, i.e., (-)-bis[methyl(4,4-dimethyl-cis-4,4a,5,6,8a,9-hexahydronaphtho[2,3-b]furan-7-yl)]disulfide.
Compound B is ent-furodysinin, i.e., (-)-4,4,7-trimethyl-cis-4,4a,5,6,8a,9-hexahydronaphtho[2,3-b]furan.
Percent reduction of parasites was the percent reduction in intestinal worm burden as compared to the untreated control. Less than 25 percent reduction recorded as zero because of test variability.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process step or steps to the objective, spirit and scope of the present invention. All such modifications are intended to be within the scope of the claims appended hereto.

What is claimed is:

1. A method for treating helminthiasis which method comprises administering to an animal in need thereof an anthelmintically effective amount of a single enantiomer or a mixture of enantiomers of a compound of the Formula (I):

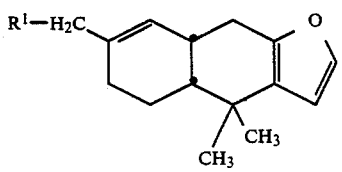 (I)

wherein
R¹ is hydrogen or —SR²,
where
R² is hydrogen, —C(O)—CH₃, or

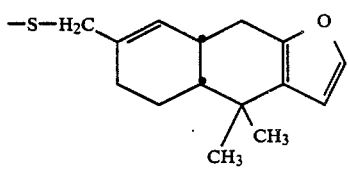

or a pharmaceutically acceptable salt thereof.

2. The method of claim 1 wherein R¹ is hydrogen.
3. The method of claim 2 wherein the compound is the levorotatory enantiomer.
4. The method of claim 1 wherein R¹ is —SR².
5. The method of claim 4 wherein R² is —C(O)—CH₃.
6. The method of claim 5 wherein the compound is the levorotatory enantiomer.
7. The method of claim 4 wherein R² is hydrogen.
8. The method of claim 4 wherein R² is

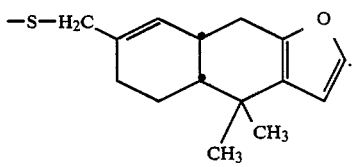

9. The method of claim 8 wherein the compound is the levorotatory enantiomer.

10. A composition for treating helminthiasis which composition comprising an anthelmintically effective amount of a single enantiomer or a mixture of enantiomers of a compound of Formula (I):

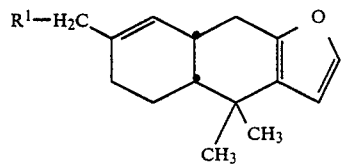

wherein
R¹ is —SR²,
where
R² is

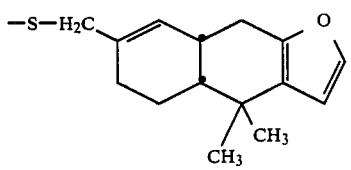

or a pharmaceutically acceptable salt thereof and a pharmaceutically acceptable excipient.

11. The composition of claim 10 wherein the compound is the levorotatory enantiomer.
12. A single enantiomer or a mixture of enantiomers of a compound of the formula:

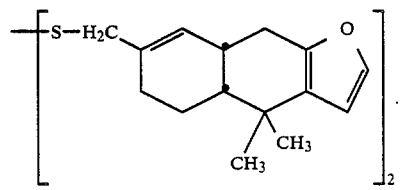

13. The compound of claim 12 wherein the compound is the levorotatory enantiomer.

* * * * *